United States Patent [19]

Algieri et al.

[11] 4,390,701

[45] Jun. 28, 1983

[54] 1-AMINO-2-[3-(3-PIPERIDINOMETHYL-PHENOXY)PROPYLAMINO]CYCLOBU-TENE-3,4-DIONE

[75] Inventors: Aldo A. Algieri, Fayetteville; Ronnie R. Crenshaw, Dewitt, both of N.Y.

[73] Assignee: Bristol-Myers Company, New York, N.Y.

[21] Appl. No.: 264,533

[22] Filed: May 18, 1981

[51] Int. Cl.³ .......................................... C07D 295/12
[52] U.S. Cl. .................................... 546/235; 424/267
[58] Field of Search ........................................ 546/235

[56] References Cited

U.S. PATENT DOCUMENTS

| | | | |
|---|---|---|---|
| 4,062,863 | 12/1977 | Ganellin et al. | 424/273 |
| 4,242,350 | 12/1980 | Yellin et al. | 424/270 |
| 4,242,351 | 12/1980 | Yellin et al. | 424/272 |

FOREIGN PATENT DOCUMENTS

| | | |
|---|---|---|
| 3640 | 8/1979 | European Pat. Off. . |
| 10418 | 4/1980 | European Pat. Off. . |
| 14057 | 8/1980 | European Pat. Off. . |
| 2001624 | 2/1979 | United Kingdom . |
| 2023133 | 12/1979 | United Kingdom . |

OTHER PUBLICATIONS

C. R. Ganellin et al., Federation Proceedings, vol. 35(8) Jun. 1976, pp. 1924–1930.
Drugs of the Future, vol. 1, No. 1 (1976) pp. 13–18.

*Primary Examiner*—Norma S. Milestone
*Attorney, Agent, or Firm*—Richard R. Lloyd

[57] ABSTRACT

Certain 1-(substituted amino)-2-(amino or substituted amino)cyclobutene-3,4-diones are potent histamine $H_2$-antagonists useful in the treatment of peptic ulcers.

2 Claims, No Drawings

1-AMINO-2-[3-(3-PIPERIDINOMETHYLPHENOXY)PROPYLAMINO]CYCLOBUTENE-3,4-DIONE

SUMMARY OF THE INVENTION

Certain substituted 1,2-diaminocyclobutene-3,4-diones of the formula

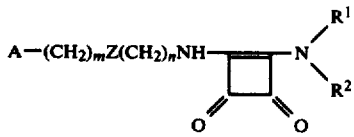

wherein A is optionally substituted phenyl, furyl or thienyl, Z is sulfur, oxygen or methylene, m is 0–2, n is 2–4 and $R^1$ and $R^2$ are as defined below, are potent histamine $H_2$-antagonists, inhibit gastric acid secretion and are useful in the treatment of peptic ulcers.

BACKGROUND AND PRIOR ART

Burimamide (IIa) was the first clinically effective $H_2$-receptor antagonist. It inhibits gastric secretion in animals and man, but oral absorption is poor.

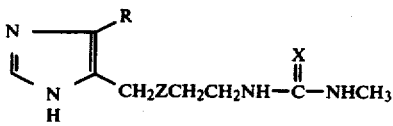

IIa; R = H, Z = $CH_2$, X = S Burimamide
b; R = $CH_3$, Z = S, X = S Metiamide
c; R = $CH_3$, Z = S, X = NCN Cimetidine Metiamide (IIb), a subsequently evaluated $H_2$-antagonist, is more potent than burimamide and is orally active in man. Clinical utility was limited, however, owing to toxicity (agranulocytosis). Cimetidine (IIc) is as effective an $H_2$-antagonist as metiamide, without producing agranulocytosis, and has recently been marketed as an anti-ulcer drug.

Reviews on the development of $H_2$-antagonists, including those discussed in the preceding paragraph, may be found in C. R. Ganellin, et al., Federation Proceedings, 35, 1924 (1976), in Drugs of the Future, 1, 13 (1976), and in references cited therein. Relevant patents are as follows:

(A) U.S. Pat. No. 4,062,863 discloses histamine $H_2$-antagonists of the formula

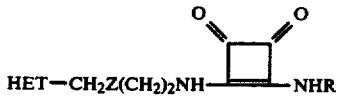

wherein R is hydrogen, (lower)alkyl or $(CH_2)_2Z'CH_2$—HET'; Z and Z' each are sulfur or methylene; and HET and HET' each are an imidazole ring optionally substituted by methyl or bromo, a pyridine ring optionally substituted by hydroxy, methoxy, chloro or bromo, a thiazole ring or an isothiazole ring, and pharmaceutically acceptable acid addition salts thereof. U.S. Pat. Nos. 4,120,968; 4,120,973 and 4,166,857 are divisionals thereof which have substantially the same disclosure.

(B) U.S. Pat. No. 4,242,350 discloses histamine $H_2$-antagonists of the formula

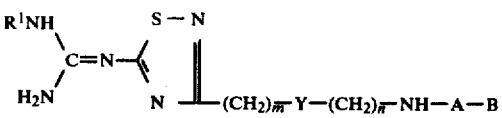

in which

Y is an oxygen or sulphur atom, a direct bond or a methylene or sulphinyl radical; m is 0 to 4 and n is 1 to 4, provided that when Y is a sulphur or oxygen atom or a sulphinyl radical m is 1 to 4, and when Y is an oxygen atom or a sulphinyl radical n is 2 to 4;

$R^1$ is a hydrogen atom or an alkyl radical of 1 to 10 carbon atoms;

A is a 3,4-dioxocyclobuten-1,2-diyl radical or a radical of the formula C=Z in which Z is an oxygen or a sulphur atom or a radical of the formula NCN, $NNO_2$, $CHNO_2$, $NCONH_2$, $C(CN)_2$, $NCOR^2$, $NCO_2R^2$, $NSO_2R^2$ or $NR^3$ in which $R^2$ is an alkyl radical of 1 to 6 carbon atoms or an aryl radical of 6 to 12 carbon atoms and $R^3$ is a hydrogen atom or an alkyl radical of 1 to 6 carbon atoms;

B is an alkoxy or alkylthio radical of 1 to 6 carbon atoms or a radical of the formula $NR^4R^5$ in which $R^4$ and $R^5$, which may be the same or different, are hydrogen atoms, alkyl radicals of 1 to 10 carbon atoms, alkenyl or alkynyl radicals of 3 to 6 carbon atoms in which the double or triple bond respectively is separated from the nitrogen atom or $NR^4R^5$ by at least one carbon atom, (primary hydroxy) alkyl or (primary amino) alkyl radicals of 2 to 6 carbon atoms or cycloalkyl radicals of 3 to 6 carbon atoms, or $R^4$ and $R^5$ are joined to form, together with the nitrogen atom to which they are attached, a 5- or 6-membered saturated ring which optionally contains an additional oxygen atom or NH radical;

and the pharmaceutically-acceptable acid-addition salts thereof.

Published European Patent Application No. 6,679 has a disclosure which is substantially the same as U.S. Pat. No. 4,242,350.

(C) U.K. Published Patent Application No. 2,001,624 discloses histamine $H_2$-antagonists of the formula

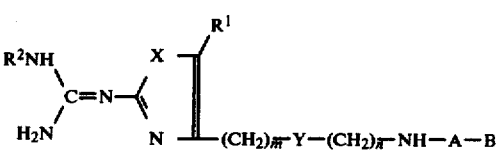

in which

X is sulphur or NH;

Y is oxygen, sulphur, a direct bond, a methylene or sulphinyl radical or a cis or transvinylene radical;

m is 0 to 4 and n is 1 to 4, provided that when Y is a sulphur, oxygen or a sulphinyl radical, m is 1 to 4 and when Y is oxygen or a sulphinyl radical n is 2 to 4;

$R^1$ is a hydrogen, halogen, or alkyl of 1 to 6 carbon atoms; $R^2$ is hydrogen, alkyl of 1 to 10 carbon atoms, alkanoyl of 1 to 6 carbon atoms or aroyl of 7 to 11 carbon atoms;

A is a 3,4-dioxocyclobuten-1,2-diyl radical or a radical of the formula C=Z in which Z is an oxygen or sulphur atom or a radical of the formula NCN, $NNO_2$, $CHNO_2$, $NCONH_2$, $C(CN)_2$, $NCOR^3$, $-NCO_2R^3$, $NSO_2R^3$ or $NR^4$ in which $R^3$ is alkyl of 1 to 6 carbon atoms or aryl of 6 to 12 carbon atoms and $R^4$ is hydrogen or alkyl of 1 to 6 carbon atoms;

B is alkoxy or alkylthio of 1 to 6 carbon atoms or a radical of the formula $NR^5R^6$ in which $R^5$ and $R^6$, which may be the same or different, are hydrogen, alkyl of 1 to 10 carbon atoms, alkenyl of 3 to 10 carbon atoms in which the double bond is separated from the nitrogen atom of $NR^5R^6$ by at least one carbon atom, cycloalkyl of 3 to 8 carbon atoms, (primary hydroxy)alkyl of 2 to 6 carbon atoms in which the oxygen atom is separated from the nitrogen atom of $NR^5R^6$ by a least two carbon atoms, alkoxyalkyl of 3 to 10 carbon atoms in which the oxygen atom is separated from the nitrogen atom of $NR^5R^6$ by at least two carbon atoms; or dialkylaminoalkyl of 4 to 10 carbon atoms in which the nitrogen atom is separated from the nitrogen atom of $NR^5R^6$ by at least two carbon atoms;

and the pharmaceutically-acceptable acid-addition salts thereof.

U.S. Pat. Nos. 4,165,377 and 4,234,735 have disclosures which are substantially the same as U.K. Pat. No. 2,001,624, except that Y may not be oxygen, sulfur or a sulfinyl radical.

U.S. Pat. No. 4,165,378 has a disclosure which is substantially the same as U.K. Pat. No. 2,001,624, except that Y may not be a direct bond, a methylene radical or a vinylene radical.

(D) U.S. Pat. No. 4,242,351 discloses histamine $H_2$-antagonists of the formula

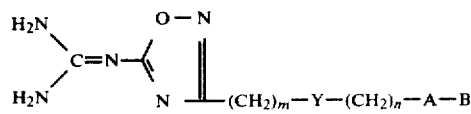

in which

Y is an oxygen or sulphur atom, a direct bond or a methylene radical;

m is 0 to 4 and n is 1 to 4, provided that when Y is a sulphur or oxygen atom m is 1 to 4, and when Y is an oxygen atom n is 2 to 4;

A is a 3,4-dioxocyclobuten-1,2-diyl radical or a radical of the formula C=Z in which Z is an oxygen or sulphur atom or a radical of the formula NCN, $NNO_2C$-$HNO_2$, $NCONH_2$, $C(CN)_2$, or $NCOR^1$, $NCO_2R^1$, $NSO_2R^1$ or $NR^2$ in which $R^1$ is an alkyl radical of 1 to 6 carbon atoms or an aryl radical of 6 to 12 carbon atoms and $R^2$ is a hydrogen atom or an alkyl radical of 1 to 6 carbon atoms;

B is an alkoxy or alkylthio radical of 1 to 6 carbon atoms or a radical of the formula $NHR^3$ in which $R^3$ is a hydrogen atom or an alkyl radical of 1 to 10 carbon atoms;

and the pharmaceutically-acceptable acid addition salts thereof.

Published European Patent Application No. 6,286 has a disclosure which is substantially the same as U.S. Pat. No. 4,242,351.

(E) Published European Patent Application No. 14,057 discloses histamine $H_2$-antagonists of the formula

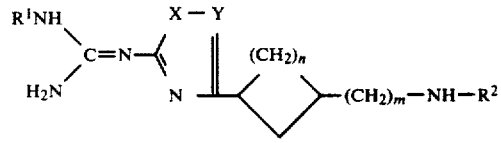

in which

X is oxygen or sulphur;

Y is nitrogen or a CH radical;

n is 1, 2, 3 or 4;

m is 0 or 1;

$R^1$ is hydrogen, alkyl of 1 to 6 carbon atoms or alkoxyalkyl of 3 to 10 carbon atoms in which the oxygen atom is separated from the nitrogen atom of the guanidine residue by at least two carbon atoms;

$R^2$ is a radical of the formula -A-B in which A is a 3,4-dioxocyclobuten-1,2-diyl radical or a radical of the formula C=Z in which Z is oxygen, sulphur or a radical of the formula NCN, $NNO_2$, $CHNO_2$, $NCONH_2$, $C(CN)_2$, $NCOR^3$, $NCO_2R^3$ or $NR^4$ in which $R^3$ is alkyl of 1 to 6 carbon atoms, phenyl or a monocyclic heteroaromatic ring containing one or two hetero atoms selected from oxygen, nitrogen and sulphur and $R^4$ is hydrogen or alkyl of 1 to 6 carbon atoms;

B is alkyl, alkoxy or alkylthio of 1 to 6 carbon atoms or a radical of the formula $NHR^5$ in which $R^5$ is hydrogen or alkyl of 1 to 6 carbon atoms, alkenyl or alkynyl of 3 to 10 carbon atoms in which the double or triple bond is separated from the nitrogen atom of $NHR^5$ by at least one carbon atom, cycloalkyl of 3 to 6 carbon atoms, (primary hydroxy)alkyl or (primary amino)alkyl of 2 to 6 carbon atoms, heteroalkyl of 1 to 6 carbon atoms, alkoxyalkyl of 3 to 6 carbon atoms in which the oxygen atom is separated from the nitrogen atom of $NHR^5$ by at least two carbon atoms, phenylalkyl or monocyclic aromatic heterocyclalkyl in which the alkyl part is of 1 to 6 carbon atoms, the phenyl ring carries an optional halogen and the heterocyclic ring contains one or two hetero atoms selected from oxygen, nitrogen and sulphur, or $R^5$ is a benzoylaminoalkyl or benzenesulphonylaminoalkyl in which the alkyl part is of 2 to 6 carbon atoms and the benzene ring carries an optional chlorine substituent, or a radical of the formula:

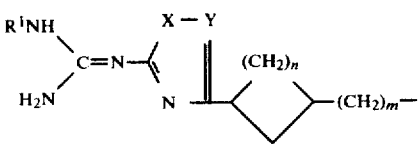

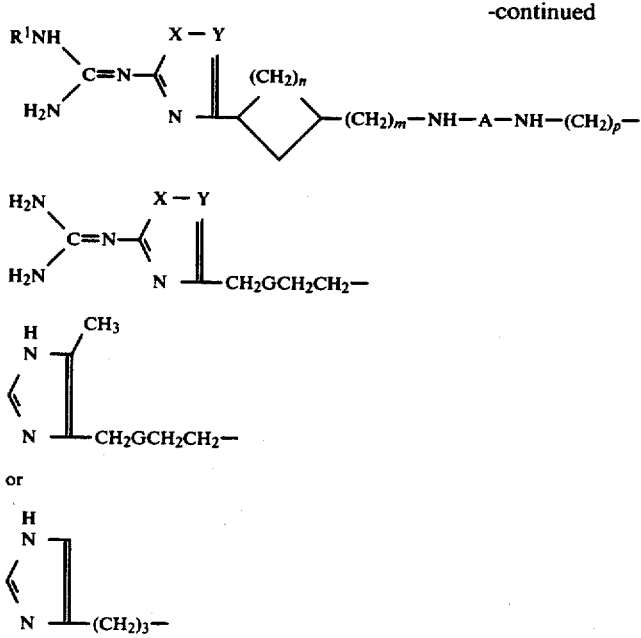

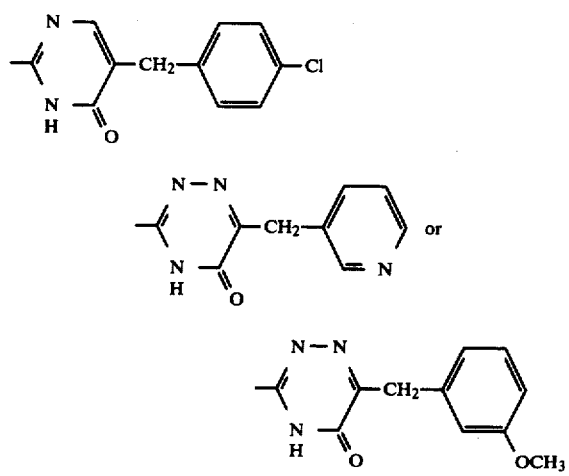

in which X, Y, n, m and $R^1$ have the meanings given above, p is 2 to 12 and G is sulphur or methylene; or $R^2$ is a radical of the formula:

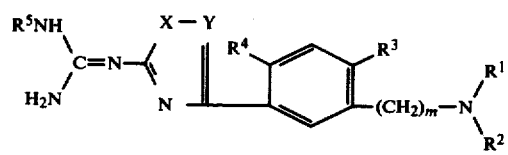

and the pharmaceutically acceptable acid addition salts thereof.

(F) Published Eureopean Patent Application No. 3,640 discloses histamine $H_2$-antagonists of the formula

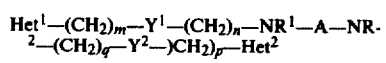

in which

X is oxygen or sulphur;

Y is nitrogen or a radical of the formula CH or $CCH_3$;

m is 0 or 1;

$R^1$ is hydrogen and $R^2$ is cyano, trifluoroacetyl, alkanoyl of 1 to 6 carbon atoms or 4,5-dihydro-4-oxothiazol-2-yl, or —$R^2$ is a radical of the formula —A—B in which A is a 3,4-dioxocyclobuten-1,2-diyl radical or a radical of the formula C=Z in which Z is oxygen, sulphur or a radical of the formula NCN, $NNO_2$, $CHNO_2$, $NCONH_2$, $C(CN)_2$, $NCOR^6$, $NCO_2R^6$, $NSO_2R^6$ or $NR^7$ in which $R^6$ is alkyl of 1 to 6 carbon atoms and $R^7$ is a hydrogen or alkyl of 1 to 6 carbon atoms and B is alkyl, alkoxy or alkylthio of 1 to 6 carbon atoms or a radical of the formula $NR^8R^9$ in which $R^8$ and $R^9$, which may be the same or different, are hydrogen, alkyl of 1 to 10 carbon atoms, alkenyl or alkynyl of 3 to 10 carbon atoms in which the double or triple bond is separated from the nitrogen atom of $NR^8R^9$ by at least one carbon atom, (primary hydroxy)alkyl of 2 to 6 carbon atoms, alkoxyalkyl of 3 to 10 carbon atoms in which the oxygen atom is separated from the nitrogen atom of $NR^8R^9$ by at least two carbon atoms, or pyridylmethyl radicals, or, when $R^9$ is hydrogen, $R^8$ is 2-[(5-dimethylaminomethylfuran-2-yl)methylthio]ethylamino, or $R^8$ and $R^9$ may be joined together to form a 5- or 6-membered non-aromatic ring which optionally contains an additional nitrogen or oxygen atom; or $R^1$ and $R^2$, taken together represent an imidazolidin-2-ylidene radical:

$R^3$ is hydrogen or fluorine;

$R^4$ is hydrogen or, when $R^3$ is hydrogen, $R^4$ is halogen or methyl;

$R^5$ is hydrogen, alkyl of 1 to 6 carbon atoms or alkoxyalkyl of 3 to 10 carbon atoms in which the oxygen atom is separated from the nitrogen atom of the guanidine residue by at least two carbon atoms;

and the pharmaceutically-acceptable acid-addition salts thereof.

(G) Published European Patent Application No. 10,418 discloses histamine $H_2$-antagonists of the formula $Het^1$—$(CH_2)_m$—$Y^1$—$(CH_2)_n$—$NR^1$—A—$NR^2$—$(CH_2)_q$—$Y^2$—$)CH_2)_p$—$Het^2$ in which $Y^1$ and $Y^2$, which may be the same or different, are oxygen, sulphur, direct bonds or methylene or sulphinyl radicals; m and p, which may be the same or different, are 0 to 4, and n and q, which may be the same or different, are 1 to 4, provided that when $Y^1$ or $Y^2$ is oxygen, sulphur or a sulphinyl radical, m or p respectively is 1 to 4 and provided that when $Y^1$ or $Y^2$ is oxygen or a sulphinyl radical, n or q respectively is 2 to 4;

one of $R^1$ and $R^2$ is hydrogen and the other is a hydrogen or alkyl of 1 to 6 carbon atoms;

A is a 3,4-dioxocyclobuten-1,2-diyl radical or a radical of the formula C=Z in which Z is sulphur, oxygen or a radical of the formula NCN, $NNO_2$, $CHNO_2$, $NCONH_2$, $C(CN)_2$, $NCOR^3$, $NCO_2R^3$, $NSO_2R^3$ or $NR^4$ in which $R^3$ is alkyl of 1 to 6 carbon atoms or aryl of 6 to 12 carbon atoms and $R^4$ is hydrogen or alkyl of 1 to 6 carbon atoms, or when $R^1$ and $R^2$ are both hydrogen —A— represents a radical of the formula:

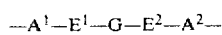

in which $A^1$ and $A^2$, which may be the same or different, are 3,4-dioxocyclobuten-1,2-diyl radicals or radicals of the formula C=$Z^1$ and C=$Z^2$ respectively in which $Z^1$ and $Z^2$, which may be the same or different, have one of the values given above for Z, $E^1$ and $E^2$, which may be the same or different, are oxygen, sulphur or NH radicals optionally substituted by alkyl of 1 to 10 carbon atoms, alkenyl or alkynyl of 3 to 10 carbon atoms in which the double or triple bond respectively is separated from the nitrogen atom to which the radical is attached by at least one carbon atom, cycloalkyl of 3 to 8 carbon atoms, (primary hydroxy)alkyl of 2 to 6 carbon atoms, alkoxyalkyl of 3 to 10 carbon atoms in which the oxygen atom is separated from the nitrogen atom to which the radical is attached by at least two carbon atoms, or alkylamino or dialkylamino of 3 to 10 and 4 to 10 carbon atoms respectively in which the nitrogen atom is separated from the nitrogen atom to which the radical is attached by at least two carbon atoms, and G is alkylene of 2 to 12 carbon atoms, alkenylene or alkynylene of 4 to 12 carbon atoms in which the double and triple bonds respectively are separated from $E^1$ and $E^2$ by at least one carbon atom, or hydroxyalkylene of 3 to 12 carbon atoms in which the hydroxy substituent is carried on a carbon atom which is separated from $E^1$ and $E^2$ by at least one carbon atom;

$Het^1$ is an oxazol-4-yl, thiazol-4-yl or imidazol-4-yl radical substituted in the 2-position by a radical of the formula:

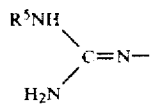

or $Het^1$ is a 1,2,4-thiadiazol-3-yl or 1,2,4-oxadiazol-3-yl radical substituted in the 5-position by a radical of the formula III, in which $R^5$ is hydrogen, alkyl of 1 to 10 carbon atoms, alkanoyl of 1 to 6 carbon atoms or aroyl of 7 to 11 carbon atoms;

$Het^2$ is one of the values given above for $Het^1$ or is an unfused nitrogen-containing 5- or 6-membered monocyclic heterocyclic ring which is optionally substituted by alkyl or alkoxy of 1 to 6 carbon atoms, hydroxy, trifluoromethyl, hydroxymethyl, amino or halogen, or $Het^2$ is a radical of the formula:

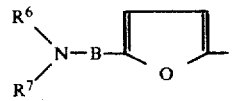

in which

B is straight- or branched-chain alkylene of 1 to 6 carbon atoms and $R^6$ and $R^7$, which may be the same or different, are hydrogen, alkyl of 1 to 8 carbon atoms, alkenyl or cycloalkyl of 3 to 8 carbon atoms, alkoxyalkyl, alkylaminoalkyl or dialkylaminoalkyl of 3 to 10 carbon atoms in which the oxygen and nitrogen atoms respectively are separated from the nitrogen atom of $NR^6R^7$ by at least two carbon atoms, or phenylalkyl of 7 to 12 carbon atoms optionally substituted on the phenyl ring by alkyl or alkoxy of 1 to 6 carbon atoms or by halogen, or $R^6$ and $R^7$ may be joined together to form a 5- or 6-membered saturated ring which may optionally contain an oxygen or additional nitrogen atom, the additional nitrogen atom being substituted by a hydrogen atom or an alkyl radical of 1 to 6 carbon atoms;

provided that when $R^1$ and $R^2$ are both hydrogen and A is C=NH, $Y^1$ and/or $Y^2$ is a sulphur atom, and then when $R^1$ and $R^2$ are both hydrogen, A is C=NH and $Het^2$ is imidazole, the number of atoms in the chain represented by:

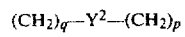

is at least four;

and the pharmaceutically-acceptable acid addition salts thereof.

(H) U.K. Published Patent Application No. 2,023,133 discloses histamine $H_2$-antagonists of the formula

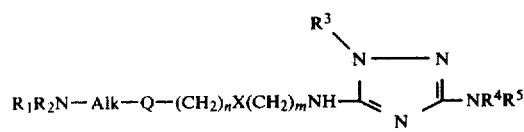

wherein $R_1$ and $R_2$ are independently hydrogen, alkyl, cycloalkyl, alkenyl, alkynyl, aralkyl, trifluoroalkyl or alkyl substituted by hydroxy, alkoxy, amino, alkylamino, dialkylamino or cycloalkyl, or $R_1$ and $R_2$, taken together with the nitrogen to which they are attached, may be a 5- to 10-membered alicyclic heterocyclic ring which may be saturated or may contain at least one double bond, which may be substituted by one or more alkyl groups or a hydroxy group and/or which may contain another heteroatom; Alk is a straight or branched alkylene chain of 1–6 carbon atoms; Q is a furan or thiophene ring incorporated into the molecule via the 2- and 5-positions, the furan ring optionally bearing a further substituent $R_7$ adjacent the $R_1R_2N$—Alk— group, or Q is a benzene ring incorporated into the molecule via its 1- and 3- or 1- and 4-positions; $R_7$ is halogen, alkyl (which may be substituted by hydroxy or alkoxy);

X is methylene, oxygen, sulfur or >N—$R^6$ in which $R^6$ is hydrogen or methyl; n is 0, 1 or 2; m is 2, 3 or 4; $R_3$ is hydrogen, alkyl, alkenyl, aralkyl, hydroxyalkyl having at least two carbon atoms, alkoxyalkyl or aryl; and $R_4$ and $R^5$ are independently hydrogen, alkyl, alkyl substituted by hydroxy or $C_{1-3}$alkoxy, alkenyl, aralkyl or heteroaralkyl, or $R_4$ and $R_5$ taken together with the nitrogen to which they are attached, may be a 5- to 7-membered saturated heterocyclic ring which may contain another heteroatom or the group $>NR^6$, or $R_4$ and $R_5$ taken together may be the group $>CR_8R_9$ wherein $R_8$ is aryl or heteroaryl and $R_9$ is hydrogen or alkyl;

and physiologically acceptable salts and hydrates thereof.

COMPLETE DISCLOSURE

This application relates to histamine $H_2$-antagonists which are effective inhibitors of gastric acid secretion in animals, including man, which are useful in the treatment of peptic ulcers and other conditions caused or exacerbated by gastric acidity, and which have the formula

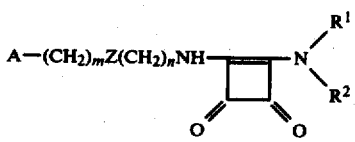

wherein $R^1$ and $R^2$ each are independently hydrogen or (lower)alkyl, and, when $R^1$ is hydrogen, $R^2$ also may be allyl, propargyl, cyclo(lower)alkyl(lower)alkyl, cyclo(-lower)alkyl, cyano(lower)alkyl, 2-fluoroethyl, 2,2,2-trifluoroethyl, hydroxy, 2,3-dihydroxypropyl,

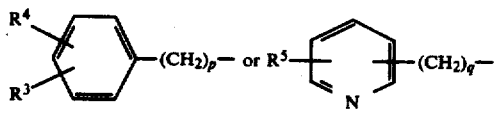

in which
p is an integer of from 1 to 6 inclusive, q is an integer of from 1 to 6 inclusive, $R^3$ and $R^4$ each are independently hydrogen, (lower)alkyl, hydroxy, (lower)alkoxy or halogen, and, when $R^3$ is hydrogen, $R^4$ also may be trifluoromethyl, or $R^3$ and $R^4$, taken together, may be methylenedioxy, $R^5$ is hydrogen, (lower)alkyl, (lower)alkoxy, hydroxy, amino or halogen;
m is an integer of from 0 to 2 inclusive;
n is an integer of from 2 to 4 inclusive;
Z is sulfur, oxygen or methylene; and
A is

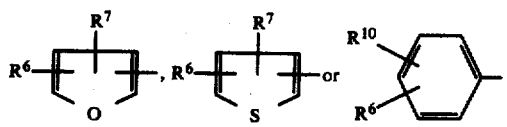

in which $R^6$ is hydrogen, (lower)alkyl, (lower)alkoxy or halogen, and $R^7$ is hydrogen or

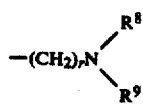

in which r is an integer of from 0 to 4 inclusive, and $R^8$ and $R^9$ each are independently hydrogen, (lower)alkyl, allyl, propargyl, (lower)alkoxy(lower)alkyl in which the (lower)alkoxy moiety is at least two carbon atoms removed from the nitrogen atom, cyclo(lower)alkyl, or phenyl(lower)alkyl, provided that $R^8$ and $R^9$ may not both be cyclo(lower)alkyl; or $R^8$ and $R^9$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino or octamethyleneimino; and $R^{10}$ is the same as $R^7$ or is

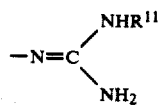

in which $R^{11}$ is hydrogen or (lower)alkyl;
or a nontoxic, pharmaceutically acceptable salt, hydrate, solvate or N-oxide thereof.

This application also relates to processes for the preparation of the compounds of Formula I and to intermediates in the preparation of the compounds of Formula I.

The present invention includes within its scope all possible tautomeric forms, geometric isomers, optical isomers and zwitterionic forms of the compounds of Formula I, as well as mixtures thereof. As used herein and in the claims, the terms "(lower)alkyl" and "(lower)alkoxy" mean straight or branched chain alkyl or alkoxy groups containing from 1 to 6 carbon atoms. Preferably these groups contain from 1 to 4 carbon atoms and, most preferably, they contain 1 or 2 carbon atoms. The term "cyclo(lower)alkyl", as used herein and in the claims, means a cycloalkyl ring containing from 3 to 7 carbon atoms and preferably from 3 to 6 carbon atoms. Unless otherwise specified in the particular instance, the term "halogen" as used herein and in the claims is intended to include chloride, fluorine, bromine and iodine. The term "nontoxic pharmaceutically acceptable salts" is intended to include salts of the compounds of Formula I with any nontoxic pharmaceutically acceptable acid. Such acids are well known and include hydrochloric, hydrobromic, sulfuric, sulfamic, phosphoric, nitric, maleic, fumaric, succinic, oxalic, benzoic, methanesulfonic, tartaric, citric, camphorsulfonic and the like. The salts are made by methods known in the art.

The compounds of Formula I may be prepared by various alternative procedures, utilizing as a starting material a compound of the formula

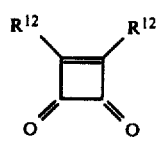

II in which $R^{12}$ is a good leaving group such as halogen, phenoxy, substituted phenoxy, alkoxy or the like. Suitable leaving groups are well known to those skilled in the art. Preferably, $R^{12}$ is (lower)alkoxy, and especially methoxy.

The compounds of Formula I may be prepared from a compound of Formula II by various alternative reaction schemes. Some of the intermediate compounds are themselves novel.

Reaction Scheme 1

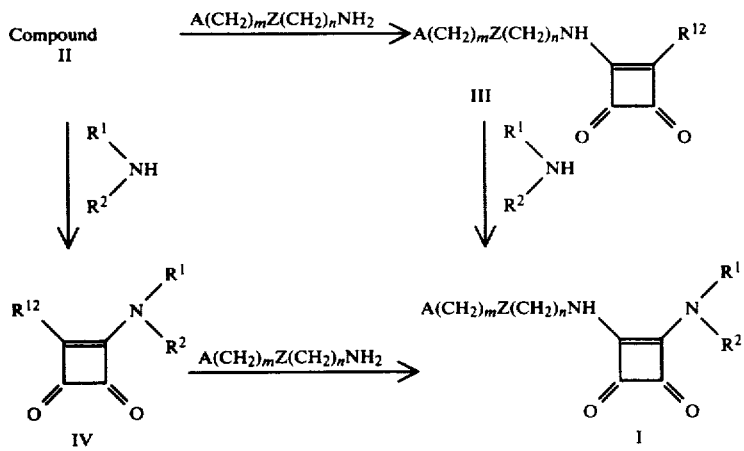

The reactions are conducted in an inert organic solvent; we find methanol to be a convenient and readily available solvent. The reaction temperature is not critical. Most starting materials are quite reactive and we prefer to conduct the reaction at a temperature below room temperature, e.g. 0°–10° C. With some less reactive compounds it is convenient to conduct the reaction at room temperature. Sometimes it is desirable to subsequently raise the temperature of the reaction mixture (e.g. to 50°–60° C.) to complete the reaction.

Reaction Scheme 2

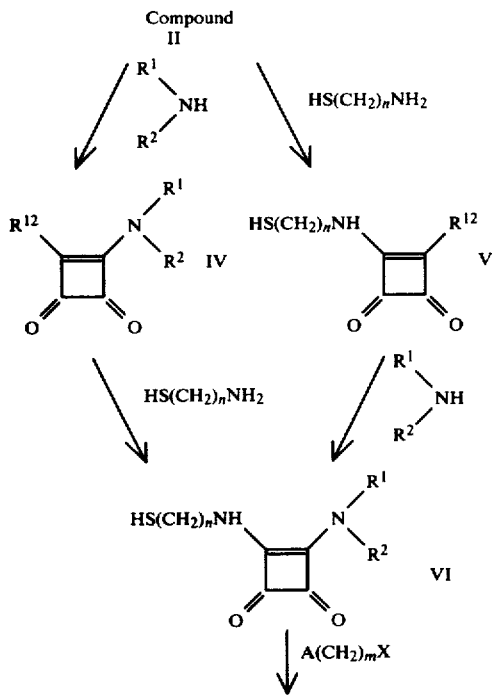

-continued
Reaction Scheme 2

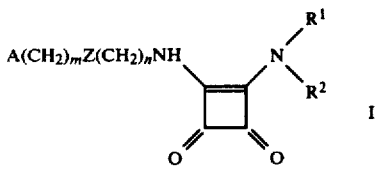

In Reaction Scheme 2, X is a conventional leaving group such as fluoro, chloro, bromo, iodo, $-O_3SR^{13}$ in which $R^{13}$ is (lower)alkyl [e.g. methanesulfonate], aryl or substituted aryl [e.g. benzenesulfonate, p-bromobenzenesulfonate or p-toluenesulfonate], $-O_3SF$, acetoxy or 2,4-dinitrophenoxy. For convenience and economy we prefer to utilize a compound in which X is chloro. The reaction conditions for the preparation of the compounds of Formula IV, V and VI are as described for Reaction Scheme 1. The reaction of the compound of Formula VI with $A(CH_2)_mX$ may be conducted in any inert organic solvent such as an alkanol, acetonitrile, dimethylformamide, dimethylsulfoxide, acetone or the like. We prefer to conduct the reaction is an alkanol such as methanol, ethanol or isopropanol. The reaction temperature is not critical; the reaction may be conducted at temperatures of from about 0° to about 200° C. At low temperatures the reaction is slow, while high temperatures normally lead to less pure products due to decomposition and the formation of side-products. We normally prefer to conduct the reaction at room temperature. The reaction of the compound of Formula VI with $A(CH_2)_mX$ to produce the compound of Formula I preferably is conducted in the presence of a base, which facilitates the reaction by acting as an acid acceptor. Suitable bases include, for example, NaOH, KOH, LiOH, triethylamine, dimethylaniline, sodium ethoxide and the like.

In a preferred embodiment of the invention the compounds of Formula I have the structure

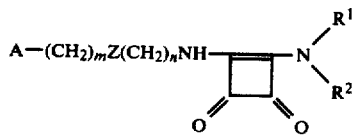

wherein $R^1$ and $R^2$ each are independently hydrogen or (lower)alkyl, and, when $R^1$ is hydrogen, $R^2$ also may be allyl, propargyl, cyclo(lower)alkyl(lower)alkyl,

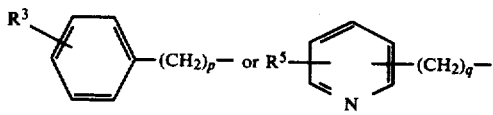

in which p and q each are independently an integer of from 1 to 6 inclusive and $R^3$ and $R^5$ each are hydrogen, (lower)alkyl or (lower)alkoxy;

m is an integer of from 0 to 2 inclusive;
n is an integer of from 2 to 4 inclusive;
Z is sulfur, oxygen or methylene; and
A is

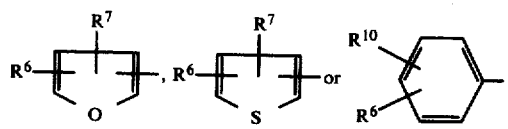

in which $R^6$ is hydrogen, (lower)alkyl or (lower)alkoxy, and $R^7$ is hydrogen or

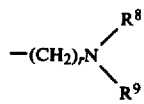

in which r is an integer of from 0 to 4 inclusive, and $R^8$ and $R^9$ each are independently hydrogen or (lower)alkyl; or, $R^8$ and $R^9$, taken together with the nitrogen atom to which they are attached, may be pyrrolidino, methylpyrrolidino, morpholino, thiomorpholino, piperidino, methylpiperidino, N-methylpiperazino, homopiperidino, heptamethyleneimino or octamethyleneimino; and $R^{10}$ is the same as $R^7$ or is

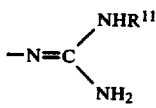

in which $R^{11}$ is hydrogen or (lower)alkyl;

or a nontoxic, pharmaceutically acceptable salt, hydrate, solvate or N-oxide thereof.

In another preferred embodiment of the invention, the compounds of Formula I have the structure

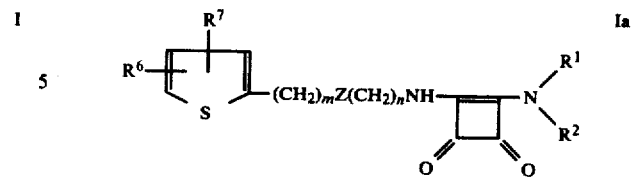

wherein $R^1$ and $R^2$ each are independently hydrogen or (lower)alkyl;

m is an integer of from 0 to 2 inclusive;
n is an integer of from 2 to 4 inclusive;
Z is sulfur, oxygen or methylene;
$R^6$ is hydrogen or (lower)alkyl; and
$R^7$ is hydrogen or

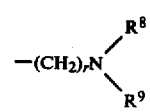

in which r is an integer of from 0 to 4 inclusive, and $R^8$ and $R^9$ each are independently hydrogen or (lower)alkyl; or $R^8$ and $R^9$, taken together with the nitrogen atom to which they are attached, may be pyrrolidino, methylpyrrolidino, morpholino, thiomorpholino, piperidino, methylpiperidino, N-methylpiperazino, homopiperidino, heptamethyleneimino or octamethyleneimino;

or a nontoxic, pharmaceutically acceptable salt, hydrate, solvate or N-oxide thereof.

In another preferred embodiment of the invention, the compounds of Formula I have the structure

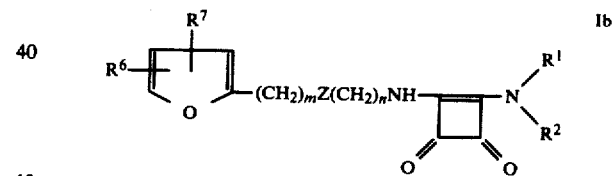

wherein $R^1$ and $R^2$ each are independently hydrogen or (lower)alkyl;

m is an integer of from 0 to 2 inclusive;
n is an integer of from 2 to 4 inclusive;
Z is sulfur, oxygen or methylene;
$R^6$ is hydrogen or (lower)alkyl; and
$R^7$ is hydrogen or

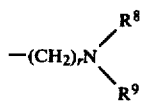

in which r is an integer of from 0 to 4 inclusive, and $R^8$ and $R^9$ each are independently hydrogen or (lower)alkyl; or $R^8$ and $R^9$, taken together with the nitrogen atom to which they are attached, may be pyrrolidino, methylpyrrolidino, morpholino, thiomorpholino, piperidino, methylpiperidino, N-methylpiperazino, homopiperidino, heptamethyleneimino or octamethyleneimino;

or a nontoxic, pharmaceutically acceptable salt, hydrate, solvate or N-oxide thereof.

In another preferred embodiment of the invention, the compounds of Formula I have the structure

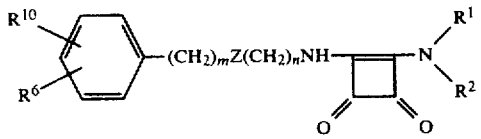

wherein

R$^1$ and R$^2$ each are independently hydrogen or (lower)alkyl;

m is an integer of from 0 to 2 inclusive;
n is an integer of from 2 to 4 inclusive;
Z is sulfur, oxygen or methylene;
R$^6$ is hydrogen or (lower)alkyl; and
R$^{10}$ is hydrogen,

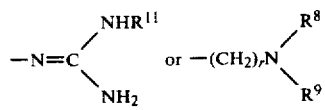

in which R$^{11}$ is hydrogen or (lower)alkyl, R$^8$ and R$^9$ each are independently hydrogen or (lower)alkyl; or R$^8$ and R$^9$, taken together with the nitrogen atom to which they are attached, may be pyrrolidino, methylpyrrolidino, morpholino, thiomorpholino, piperidino, methylpiperidino, N-methylpiperazino, homopiperidino, heptamethyleneimino or octamethyleneimino;

or a nontoxic, pharmaceutically acceptable salt, hydrate, solvate or N-oxide thereof.

As presently envisaged, the particularly preferred compounds of Formula I are (a) 1-amino-2-[3-(3-piperidinomethylphenoxy)-propylamino]cyclobutene-3,4-dione, or a nontoxic pharmaceutically acceptable salt, hydrate, solvate or N-oxide thereof (and particularly the hydrochloride thereof), (b) 1-amino-2-{2-[(5-dimethylaminomethyl-2-furyl)-methylthio]ethylamino}cyclobutene-3,4-dione, or a nontoxic pharmaceutically acceptable salt, hydrate, solvate or N-oxide thereof, and (c) 1-amino-2-{2-[(5-dimethylaminomethyl-2-thienyl)methylthio]ethylamino}cyclobutene-3,4-dione, or a nontoxic pharmaceutically acceptable salt, hydrate, solvate or N-oxide thereof.

In another aspect, this invention relates to novel intermediates of the formula

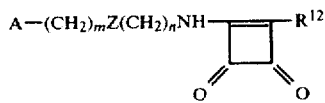

wherein

R$^{12}$ is a conventional leaving group selected from halogen, phenoxy, substituted phenoxy and alkoxy;
m is an integer of from 0 to 2 inclusive;
n is an integer of from 2 to 4 inclusive;
Z is sulfur, oxygen or methylene; and
A is

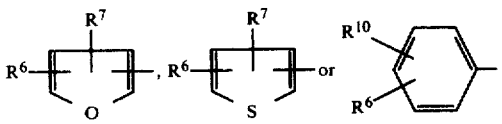

in which R$^6$ is hydrogen, (lower)alkyl, (lower)alkoxy or halogen, and R$^7$ is hydrogen or

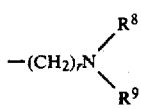

in which r is an integer of from 0 to 4 inclusive, and R$^8$ and R$^9$ each are independently hydrogen, (lower)alkyl, allyl, propargyl, (lower)alkoxy(lower)alkyl in which the (lower)alkoxy moiety is at least two carbon atoms removed from the nitrogen atom, cyclo(lower)alkyl, or phenyl(lower)alkyl, provided that R$^8$ and R$^9$ may not both be cyclo(lower)alkyl; or R$^8$ and R$^9$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino or octamethyleneimino; and R$^{10}$ is the same as R$^7$ or is

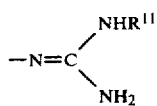

in which R$^{11}$ is hydrogen or (lower)alkyl.

A preferred embodiment of the intermediates of Formula III are those having the structure

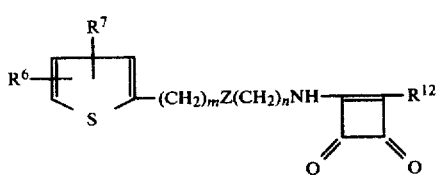

wherein

R$^{12}$ is a conventional leaving group selected from halogen, phenoxy, substitituted phenoxy and (lower)alkoxy;
m is an integer of from 0 to 2 inclusive;
n is an integer of from 2 to 4 inclusive;
Z is sulfur, oxygen or methylene;
R$^6$ is hydrogen or (lower)alkyl; and
R$^7$ is hydrogen or

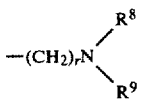

in which r is an integer of from 0 to 4 inclusive, and R$^8$ and R$^9$ each are independently hydrogen or (lower)alkyl; or R$^8$ and R$^9$, taken together with the nitrogen atom to which they are attached, may be pyrrolidino, methylpyrrolidino, morpholino, thiomorpholino, piperidino, methylpiperidino, N-methylpiperazino, homopiperidino, heptamethyleneimino or octamethyleneimino.

Another preferred embodiment of the intermediates of Formula III are those having the structure

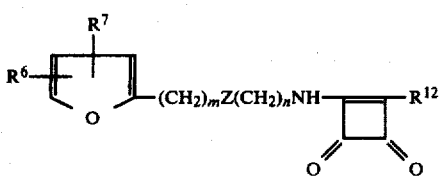   IIIb wherein

R$^{12}$ is a conventional leaving group selected from halogen, phenoxy, substituted phenoxy and (lower)alkoxy;

m is an integer of from 0 to 2 inclusive;
n is an integer of from 2 to 4 inclusive;
Z is sulfur, oxygen or methylene;
R$^6$ is hydrogen or (lower)alkyl; and
R$^7$ is hydrogen or

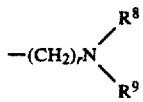

in which r is an integer of from 0 to 4 inclusive, and R$^8$ and R$^9$ each are independently hydrogen or (lower)alkyl; or R$^8$ and R$^9$, taken together with the nitrogen atom to which they are attached, may be pyrrolidino, methylpyrrolidino, morpholino, thiomorpholino, piperidino, methylpiperidino, N-methylpiperazino, homopiperidino, heptamethyleneimino or octamethyleneimino.

Another preferred embodiment of the intermediates of Formula III are those having the structure

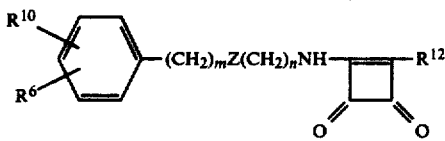   IIIc wherein

R$^{12}$ is a conventional leaving group selected from halogen, phenoxy, substituted phenoxy and (lower)alkoxy;

m is an integer of from 0 to 2 inclusive;
n is an integer of from 2 to 4 inclusive;
Z is sulfur, oxygen or methylene;
R$^6$ is hydrogen or (lower)alkyl; and
R$^{10}$ is hydrogen,

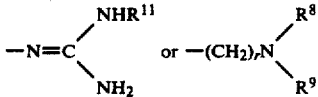

in which R$^{11}$ is hydrogen or (lower)alkyl, R$^8$ and R$^9$ each are independently hydrogen or (lower)alkyl; or R$^8$ and R$^9$, taken together with the nitrogen atom to which they are attached, may be pyrrolidino, methylpyrrolidino, morpholino, thiomorpholino, piperidino, methylpiperidino, N-methylpiperazino, homopiperidino, heptamethyleneimino or octamethyleneimino.

As presently envisaged, the most preferred intermediates of Formula III are (a)  1-methoxy-2-[3-(3-piperidinomethylphenoxy)-propylamino]cyclobutene-3,4-dione, (b)  1-methoxy-2-{2-[(5-dimethylaminomethyl-2-furyl)methylthio]ethylamino}cyclobutene-3,4-dione, and (c)  1-methoxy-2-{2-[(5-dimethylaminomethyl-2-thienyl)methylthio]ethylamino}cyclobutene-3,4-dione.

The starting materials of Formula II used in the preparation of the compounds of this invention are either known or are prepared by methods known in the art. See, for example, the extensive review article by A. H. Schmidt in Synthesis, Pages 961–994 (December 1980) and references cited therein.

For therapeutic use, the pharmacologically active compounds of Formula I will normally be administered as a pharmaceutical composition comprising as the (or an) essential active ingredient at least one such compound in its basic form or in the form of a nontoxic pharmaceutically acceptable acid addition salt, in association with a pharamaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or non-aqueous liquid suspension. The pharmaceutical compositions are prepared by conventional techniques appropriate to the desired preparation.

The dosage of the compounds of this invention will depend not ony on such factors as the weight of the patient, but also on the degree of gastric acid inhibition desired and the potency of the particular compound being utilized. The decision as to the particular dosage to be employed is within the discretion of the physician. In the Heidenhain Pouch Dog test described below, cimetidine has an oral ED$_{50}$ of approximately 3.3 $\mu$moles/kg. The usual human adult oral dose of cimetidine is 300 mg, given four times a day. The usual human adult starting oral dosages of the compounds of this invention are readily determined from their oral ED$_{50}$ in this same test. Thus, if the oral ED$_{50}$ is 0.33 $\mu$moles/kg, the usual starting oral dosage would be approximately 30 mg, given four times a day, etc. Similar calculations may be made for iv dosages. These starting dosages (and the number of times administered per day) may, of course, be varied by titration of the dosage to the particular circumstances of the specific patient. With the preferred compounds of this invention, each oral dosage unit will contain the active ingredient in an amount of from about 5 mg to about 300 mg, and most preferably from about 10 mg to about 100 mg. The active ingredient will preferably be administered in equal doses from two to four times a day.

Histamine H$_2$-receptor antagonists have been shown to be effective inhibitors of gastric secretion in animals and man, Brimblecombe et al., J. Int. Med. Res., 3, 86 (1975). Clinical evaluation of the histamine H$_2$-receptor antagonist cimetidine has shown it to be an effective therapeutic agent in the treatment of peptic ulcer disease, Gray et al., Lancet, 1, 8001 (1977). Two of the standard animal models for determining gastric antisecretory activity of histamine $H_2$-antagonists are the Gastric Fistula Rat and the Heidenhain Pouch Dog. The $ED_{50}$'s for some of the compounds of this invention in these two animal models are given in Tables 1 and 2, below.

DETERMINATION OF GASTRIC ANTISECRETORY ACTIVITY IN THE GASTRIC FISTULA RAT

Male Long Evans rats weighing about 240–260 grams at the time of cannula implantation are used. The design and implantation of the stainless steel cannula into the anterior wall of the fore-stomach are carried out essentially as described by Pare et al. [Laboratory Animal Science, 27, 244 (1977)]. The fistula components are designed and the operative procedure is carried out exactly as described in the above reference. Post operatively the animals are individually housed in solid bottom cages with sawdust and are allowed food and water ad libitum throughout the entire recovery period. Animals are not used for test purposes for at least 15 days after the operative procedure.

The animals are fasted but allowed water ad libitum for 20 hours before the testing procedure is to begin. Immediately prior to collection, the cannula is opened and the stomach washed gently with 30–40 ml of warm saline or distilled water to remove any residual contents. The catheter is then screwed into the cannula in place of the plugging screw and the rat is placed in a clear plastic rectangular cage measuring 40 cm long, 15 cm wide and 13 cm high. The bottom of the cage has a slit approximately 1.5 cm wide and 25 cm long running down the center to accommodate the catheter which hangs through it. In this way the rat is not restricted and can move freely about the cage during collection periods. The remainder of the assay is carried out as described by Ridley et al. [Research Comm. Chem. Path. Pharm., 17, 365 (1977)].

Gastric secretions collected during the first hour after washing the stomach are discarded as they may be contaminated. For oral evaluation, the catheter is then removed from the cannula and replaced with the plugging screw. Water (2 ml/kg) is administered orally via gastric intubation and the animal is returned to the cage for 45 minutes. After this time the plugging screw is removed and replaced with a catheter to which a small plastic vial has been attached to collect the gastric secretions. A two hour sample is collected (this represents the control secretion), the catheter removed and replaced with the plugging screw. The test drug is now administered orally in a volume of 2 ml/kg via gastric intubation. Forty-five minutes later the plugging screw is again removed, replaced with the catheter attached to a small plastic vial and another 2 hour sample is collected. The secretions in the second sample are compared to those of the control sample in order to determine the effects of the test drug.

When test compounds are to be evaluated parenterally, the animal is injected ip or sc with the test compound vehicle in a volume of 2 ml/kg immediately after discarding the initial 60 minute collection. A two hour sample is collected (control secretion) and the animals are injected either ip or sc with the test compound in a volume of 2 ml/kg. An additional two hour sample is collected and its secretions are compared to those of the control period to determine drug effects.

The samples are centrifuged and placed in a graduated centrifuge tube for volume determination. Titratable acidity is measured by titrating a one ml sample to pH 7.0 with 0.02 N NaOH, using an Autoburet and an electrometric pH meter (Radiometer). Titratable acid output is calculated in microequivalents by multiplying the volume in milliliters by the acid concentration in milliequivalents per liter.

Results are expressed as percent inhibition relative to control readings. Dose response curves are constructed and $ED_{50}$ values are calculated by regression analyses. At least three rats are used at each dosage level and a minimum of three dosage levels are utilized for determination of a dose response curve.

DETERMINATION OF GASTRIC ANTISECRETORY ACTIVITY IN THE HEIDENHAIN POUCH DOG

Prior to surgery, hematology and blood chemistry profiles are obtained and an assessment made as to the general health of selected female dogs. Dogs are vaccinated with Tissue Vax 5 (DHLP—Pitman-Moore) and housed in general animal quarters for four weeks' observation so incipient diseases may become apparent. Dogs are fasted with water ad libitum 24 hours prior to surgery.

Anesthesia is induced with Sodium Pentothal (Abbott) 25–30 mg/kg iv. Subsequent anesthesia is maintained with methoxyflurane (Pitman-Moore). A midline linea alba incision from xiphoid to umbilicus provides good exposure and ease of closure. The stomach is pulled up into the operative field, the greater curvature stretched out at multiple points and clamps placed along the selected line of incision. The pouch is made from the corpus of the stomach so that true parietal cell juice is obtained. About 30% of the corpus volume is resected. The cannula is made of light-weight, biologically-inert material such as nylon or Delrin with dimensions and attachments after DeVito and Harkins [J. Appl. Physiol., 14, 138 (1959)]. Post operatively, dogs are medicated with antibiotics and an analgesic. They are allowed 2–3 months for recovery. Experiments are carried out in the following way: Dogs are fasted overnight (~18 hours) with water ad libitum prior to each experiment. The dogs are placed in a sling and a saphenous vein cannulated for drug administration. Histamine as the base (100 $\mu$g/kg/hr) and chlorpheniramine maleate (0.25 mg/kg/hr) are infused continuously (in a volume of 6 ml/hr) with a Harvard infusion pump.

Ninety minutes' infusion are allowed for the dogs to reach a steady state of acid output. At this time the drug or normal saline (control) is administered concomitantly with the secretagogue in a volume of 0.5 ml/kg over a 30 second period. When oral studies are to be carried out, the drug is administered via gastric gavage in a volume of 5 ml/kg. Infusion of the secretagogue is continued and 15 minute samples of the gastric juice are taken for 4.5 hours. Each sample is measured to the nearest 0.5 ml and tritratable acidity is determined by titrating a 1 ml sample to pH 7.0 with 0.2 N NaOH, using an Autoburet and an electrometric pH meter (Radiometer). Titratable acid output is calculated in microequivalents by multiplying the volume in milliliters by the acid concentration in milliequivalents per liter.

Results are expressed as percent inhibition relative to control readings. Dose response curves are constructed and $ED_{50}$ values are calculated by regression analyses.

From 3 to 5 dogs are used at each dose level and a minimum of three dosage levels are utilized for determination of a dose response curve.

Celite is a registered trademark of the Johns-Manville Products Corporation for diatomaceous earth.

In the following examples, all temperatures are given in degrees Centigrade.

TABLE 1

| Gastric Antisecretory Activity in the Gastric Fistula Rat | | |
|---|---|---|
| Compound | $ED_{50}$ sc ($\mu$moles/kg) | Potency Ratio (cimetidine = 1.0) |
| Cimetidine | 3.8 (2.3–5.5) | 1.0 |
| Compound of Example 1 | 0.029 (0.016–0.048) | 130 |
| Compound of Example 2 | ~2 | ~2 |
| Compound of Example 3 | ~4 | ~1 |

TABLE 2

| Gastric Antisecretory Activity in the Heidenhain Pouch Dog | | |
|---|---|---|
| Compound | $ED_{50}$ ($\mu$moles/kg) | Potency Ratio (cimetidine = 1.0) |
| Cimetidine | 2.18 (iv) (1.48–2.95) | 1.0 |
| Compound of Example 1 | 0.0240 (iv) (0.0169–0.0340) | 91 |
| Cimetidine | 3.29 (oral) (1.05–5.19) | 1.0 |
| Compound of Example 1 | 0.175 (oral) (0.00879–0.249) | 19 |

EXAMPLE 1

1-Amino-2-[3-(3-piperidinomethylphenoxy)-propylamino]cyclobutene-3,4-dione

A solution of 3-(3-piperidinomethylphenoxy)propylamine (from the dihydrochloride, 4.46 g; 13.9 mmoles) [prepared according to published U.K. Patent Application No. 2,023,133] in 40 ml of methanol was added all at once to a solution of 1,2-dimethoxycyclobutene-3,4-dione (1.97 g; 13.9 mmoles) in 40 ml of methanol that had been cooled to 5° in an ice-water bath. After 2 hours at ambient temperature, the solution was cooled to 5° and excess anhydrous ammonia was bubbled into the solution for 5 minutes. The mixture was stirred at ambient temperature for 18 hours and then filtered to give 4.35 g of product.

The product (4.20 g; 12.2 mmoles) was suspended in 40 ml of 95% aqueous ethanol and 6.11 ml (12.2 mmoles) of aqueous 2.0 N HCl was added with stirring. The solution was filtered through Celite, cooled at 0° for 17 hours, and then filtered to give 4.33 g of the title compound as its hydrochloride salt, mp 254°–257°.

Anal. Calc'd. for $C_{19}H_{26}ClN_3O_3$: C, 60.08; H, 6.90, N, 11.06; Cl, 9.33. Found (corr. for 0.28% $H_2O$): C, 59.73; H, 6.97; N, 11.14; Cl, 9.36.

EXAMPLE 2

1-Amino-2-{2-[(5-dimethylaminomethyl-2-furyl)methylthio]ethylamino}cyclobutene-3,4-dione A solution of 2-[(5-dimethylaminomethyl-2-furyl)methylthio]ethylamine (2.89 g; 13.5 mmoles) [prepared according to the procedure described in Belgian Pat. No. 857,388] in 30 ml of methanol was added dropwise over a period of 30 minutes to a cold (5°) stirred solution of 1,2-dimethoxycyclobutene-3,4-dione (1.92 g; 13.5 mmoles) in 50 ml of methanol. After 3 hours at ambient temperature, the solution was cooled to 5° and excess anhydrous ammonia was bubbled into the solution for 5 minutes. The mixture was stirred at ambient temperature for 18 hours and then filtered to give 2.48 g of the title compound, mp 227°–230° (dec.).

An analytical sample was prepared by recrystallization from 95% aqueous ethanol and then from methanol, and was dried in vacuo over $P_2O_5$ for 18 hours to give the title compound as a non-friable sticky solid; the NMR spectrum (100 MHz) in $d_6$ dimethylsulfoxide showed the presence of approximately 0.2 moles of methanol.

Anal. Calc'd. for $C_{14}H_{19}N_3O_3S.0.2$ $CH_4O$: C, 54.01; H, 6.32; N, 13.31; S, 10.15. Found (corr. for 0.54% $H_2O$): C, 53.72; H, 6.07; N, 14.01; S, 10.51.

EXAMPLE 3

1-Amino-2-{2-[(5-dimethylaminomethyl-2-thienyl)methylthio]ethylamino}cyclobutene-3,4-dione A solution of 2-[(5-dimethylaminomethyl-2-thienyl)-methylthio]ethylamine (2.06 g; 8.94 mmoles) [prepared according to the procedure described in Belgian Pat. No. 867,105] in 20 ml of methanol was added all at once to a cold (5°) solution of 1,2-dimethoxycyclobutene-3,4-dione (1.27 g; 8.94 mmoles) in 20 ml of methanol. After 3.5 hours at ambient temperature, the solution was cooled to 5° and excess anhydrous ammonia was bubbled into the solution for 5 minutes. The mixture was stirred for 18 hours at ambient temperature and then filtered to give 2.66 g of product. Recrystallization from 95% aqueous ethanol yielded the title compound, mp 240°–243° (dec.).

Anal. Calc'd. for $C_{14}H_{19}N_3O_2S_2$: C, 51.67; H, 5.88; N, 12.91; S, 19.70. Found: C, 51.60; H, 5.76; N, 12.97; S, 19.69.

We claim:
1. 1-Amino-2-[3-(3-piperidinomethylphenoxy)-propylamino]cyclobutene-3,4-dione, or a nontoxic pharmaceutically acceptable salt thereof,
2. 1-Amino-2-[3-(3-piperidinomethylphenoxy)-propylamino]cyclobutene-3,4-dione hydrochloride.

* * * * *